(12) United States Patent
Kim et al.

(10) Patent No.: US 8,592,192 B2
(45) Date of Patent: Nov. 26, 2013

(54) PROTEIN STABILIZATION BY DOMAIN INSERTION INTO A THERMOPHILIC PROTEIN

(75) Inventors: Jin Ryoun Kim, Jericho, NY (US); Brennal Pierre, Brooklyn, NY (US); Marc Ostermeier, Baltimore, MD (US); Chung-Sei Kim, Palisade Park, NJ (US)

(73) Assignee: Polytechnic Institute of NYU, Brooklyn, NY (US)

( * ) Notice: Subject to any disclaimer, the term of this patent is extended or adjusted under 35 U.S.C. 154(b) by 560 days.

(21) Appl. No.: 12/718,160

(22) Filed: Mar. 5, 2010

(65) Prior Publication Data

US 2010/0227374 A1 Sep. 9, 2010

Related U.S. Application Data

(60) Provisional application No. 61/158,124, filed on Mar. 6, 2009.

(51) Int. Cl.
*C12N 9/96* (2006.01)
(52) U.S. Cl.
USPC ....... 435/188; 435/69.1; 435/69.7; 435/188.5
(58) Field of Classification Search
None
See application file for complete search history.

*Primary Examiner* — Robert A Zeman
(74) *Attorney, Agent, or Firm* — Laurence P. Colton; Smith Risley Tempel Santos LLC

(57) ABSTRACT

A strategy to improve protein stability by domain insertion. TEM 1 beta-lactamase (BLA) and exo-inulinase, as model target enzymes, are inserted into a hyperthermophilic maltose binding protein from *Pyrococcus furiosus* (PfMBP). Unlike conventional protein stabilization methods that employ mutations and recombinations, the inventive approach does not require any modification on a target protein except for its connection with a hyperthermophilic protein scaffold. For that reason, target protein substrate specificity was largely maintained, which is often modified through conventional protein stabilization methods. The insertion was achieved through gene fusion by recombinant DNA techniques.

5 Claims, 3 Drawing Sheets

SEQUENCE LISTING

<160> NUMBER OF SEQ ID NOS: 2

<210> SEQ ID NO 1
<211> LENGTH: 412
<212> TYPE: PRT
<213> ORGANISM: Pyrococcus furiosus

<400> SEQUENCE: 1

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Val Val Ile Trp His Ala Met Gln Pro Asn Glu Leu Glu Val Phe Gln
        35                  40                  45

Ser Leu Ala Glu Glu Tyr Met Ala Leu Cys Pro Glu Val Glu Ile Val
    50                  55                  60

Phe Glu Gln Lys Pro Asn Leu Glu Asp Ala Leu Lys Ala Ala Ile Pro
65                  70                  75                  80

Thr Gly Gln Gly Pro Asp Leu Phe Ile Trp Ala His Asp Trp Ile Gly
                85                  90                  95

Lys Phe Ala Glu Ala Gly Leu Leu Glu Pro Ile Asp Glu Tyr Val Thr
            100                 105                 110

Glu Asp Leu Leu Asn Glu Phe Ala Pro Met Ala Gln Asp Ala Met Gln
        115                 120                 125

Tyr Lys Gly His Tyr Tyr Ala Leu Pro Phe Ala Ala Glu Thr Val Ala
    130                 135                 140

Ile Ile Tyr Asn Lys Glu Met Val Ser Glu Pro Pro Lys Thr Phe Asp
145                 150                 155                 160

Glu Met Lys Ala Ile Met Glu Lys Tyr Tyr Asp Pro Ala Asn Glu Lys
                165                 170                 175

Tyr Gly Ile Ala Trp Pro Ile Asn Ala Tyr Phe Ile Ser Ala Ile Ala
            180                 185                 190

Gln Ala Phe Gly Gly Tyr Tyr Phe Asp Asp Lys Thr Glu Gln Pro Gly
        195                 200                 205

Leu Asp Lys Pro Glu Thr Ile Glu Gly Phe Lys Phe Phe Thr Glu
    210                 215                 220

Ile Trp Pro Tyr Met Ala Pro Thr Gly Asp Tyr Asn Thr Gln Gln Ser
225                 230                 235                 240

Ile Phe Leu Glu Gly Arg Ala Pro Met Met Val Asn Gly Pro Trp Ser
                245                 250                 255

Ile Asn Asp Val Lys Lys Ala Gly Ile Asn Phe Gly Val Val Pro Leu
            260                 265                 270

Pro Pro Ile Ile Lys Asp Gly Lys Glu Tyr Trp Pro Arg Pro Tyr Gly
        275                 280                 285

Gly Val Lys Leu Ile Tyr Phe Ala Ala Gly Ile Lys Asn Lys Asp Ala
```

```
                290                 295                 300
Ala Trp Lys Phe Ala Lys Trp Leu Thr Thr Ser Glu Glu Ser Ile Lys
305                 310                 315                 320

Thr Leu Ala Leu Glu Leu Gly Tyr Ile Pro Val Leu Thr Lys Val Leu
                325                 330                 335

Asp Asp Pro Glu Ile Lys Asn Asp Pro Val Ile Tyr Gly Phe Gly Gln
                340                 345                 350

Ala Val Gln His Ala Tyr Leu Met Pro Lys Ser Pro Lys Met Ser Ala
                355                 360                 365

Val Trp Gly Gly Val Asp Gly Ala Ile Asn Glu Ile Leu Gln Asp Pro
                370                 375                 380

Gln Asn Ala Asp Ile Glu Gly Ile Leu Lys Lys Tyr Gln Gln Glu Ile
385                 390                 395                 400

Leu Asn Asn Met Gln Gly His His His His His His
                405                 410

<210> SEQ ID NO 2
<211> LENGTH: 1242
<212> TYPE: DNA
<213> ORGANISM: Pyrococcus furiosus

<400> SEQUENCE: 2
atgaaaataa aaacaggtgc acgcatcctc gcattatccg cattaacgac gatgatgttt      60
tccgcctcgg ctctcgccaa atcgaagaa ggaaaagttg ttatttggca tgcaatgcaa      120
cccaatgagc ttgaggtctt ccaaagctta gcggaagaat acatggcact ctgtccagaa      180
gttgagatag ttttgaaca aaagccaaac ttggaagatg ctcttaaggc tgcaataccc      240
acaggtcaag gtcctgacct ctttatctgg gctcacgact ggattggaaa gtttgctgag      300
gcaggattac ttgagccaat gatgaatat gtaactgaag atctccttaa cgagtttgct      360
ccaatggccc aggatgcaat gcagtataaa ggtcactact atgctctacc attcgccgct      420
gaaacagttg caataatcta caacaaagaa atggttagcg agccaccgaa aacctttgat      480
gagatgaagg caataatgga gaagtactat gatccagcaa atgagaagta tggaatagct      540
tggccaatta atgcctactt tatctcagca attgctcagg cctttggtgg ttactacttt      600
gacgacaaaa cagagcaacc gggactagat aagcctgaga caatcgaagg atttaagttc      660
ttcttcacag aaatatggcc atacatggct ccaactggag actacaacac tcaacagagt      720
atattcctcg agggtagagc cccaatgatg gttaatggtc catggagcat taacgacgtt      780
aagaaggcag aataaacctt tggagtggtt ccactacctc caataatcaa ggatggtaag      840
gagtactggc caaggcctta cggtggagtt aagttgattt acttcgcagc gggaataaag      900
aacaaggatg ctgcatggaa gttcgcaaag tggcttacca caagcgaaga gtcaattaag      960
acattggcac tagagctggg atacataccg gttcttacga aggttcttga tgatccagaa     1020
attaagaatg atccagtaat ctatggcttt ggacaagcag ttcagcacgc atacctaatg     1080
ccaaagagtc caaagatgag tgctgtttgg ggcggagttg atggggcaat taacgaaatc     1140
ctccaagatc cacaaaacgc tgacattgaa ggaatactaa agaagtatca acaagaaatc     1200
cttaacaaca tgcaaggcca tcatcaccac catcactgat aa                        1242
```

PROTEIN STABILIZATION BY DOMAIN INSERTION INTO A THERMOPHILIC PROTEIN

STATEMENT OF RELATED APPLICATIONS

Figure 1:
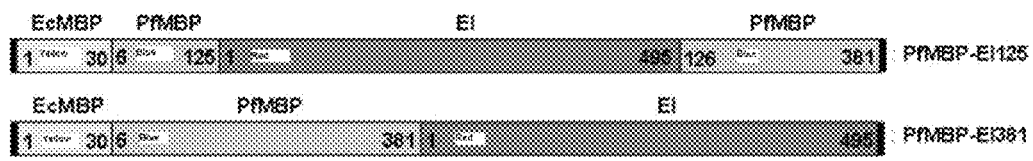

This patent application claims the benefit of U.S. provisional patent application No. 61/158,124 having a filing date of 6 Mar. 2006, which is incorporated herein in its entirety by this reference.

SEQUENCE LISTING

The instant application contains a Sequence Listing which has been submitted in ASCII format via EFS-Web and is hereby incorporated by reference in its entirety. Said ASCII copy, created on Apr. 24, 2013, is named 48467.034US_S-L.txt and is 5,589 bytes in size.

BACKGROUND OF THE INVENTION

1. Technical Field

The present invention relates generally to the field of stabilizing proteins, and more specifically to the field of stabilizing proteins without any modification of their primary sequence. The present invention further relates to stabilizing proteins by employing domain insertion of a target protein into a thermophilic scaffold protein.

2. Prior Art

High specificity and selectivity of a protein as a catalyst are of great importance in the (bio)chemical industry as these properties can reduce the number of reaction steps in synthesis and simplify product purification. For example, lipase has been employed for producing novel polymers that would otherwise be difficult to make by conventional chemical polymerization. However, despite a number of advantages over conventional chemical reactions, the progress of enzymatic reactions has been limited due to the insufficient stability of enzymes under common reaction conditions, such as the presence of organic solvents as well as high pressures and temperatures. Under these conditions, proteins unfold and lose activity significantly. In fact, limited stability is a common problem associated with most proteins.

Improvements in stability have been accomplished through rational, combinatorial and data-driven design. A large body of data has demonstrated that protein stabilization can be achieved by rational or combinatorial design or a combination of both. The rational design requires a knowledge of protein 3D structures and/or an understanding of forces and interactions affecting protein stability. Successful attempts have been reported in the rational design of highly stable proteins. Some rational protein stabilization strategies include "entropic stabilization" through rigidification by mutations, introduction of disulfide bridges, salt bridges, and clusters of aromatic-aromatic interactions, and engineering of subunit interfaces of multimeric proteins. Structural studies of extremophilic organisms and their proteins have provided significant insight into the molecular determinants of stabilization. Mesophilic proteins have been engineered to become highly stable through mutations found in corresponding thermophilic proteins. Comparative studies on a large number of naturally found or engineered stable proteins have revealed the existence of different ways of enhancing protein stability through mutations and recombinations. The combinatorial design requires construction of a diverse library and its screening to isolate variants with desired properties. A considerable amount of proteins with high stability have been identified using combinatorial design. Recently, data-driven design, where the library size is reduced by pinpointing specific residues to target based on structure and sequence information, has led to isolation of stable proteins.

Improvements in stability also have been accomplished by the addition of molecular chaperones and ligands. Molecular chaperones have been used not only for improving folding of a protein in vivo but also stability of a protein in vitro. Exposed hydrophobic surfaces, which should be buried in otherwise native protein structures, are the main targets of molecular chaperones. Addition of GroES, GroEL and ATP in vitro increased kinetic stability of alcohol dehydrogenase at 50° C. by two-fold. Similarly, the chaperone activity of aB-crystallin prevented unfolding and aggregation of citrate synthase at 45° C. Chemical chaperones, such as glycerol, trehalose and trimethylamine-N-oxide, can also be used for protein stabilization at a moderately high temperature or in the presence of denaturants. The ligand binding of proteins often enhances stability by virtue of coupling of binding with unfolding equilibrium. For instance, binding of biotin to streptavidin and anilinonaphthalene sulphonate derivatives to bovine serum albumin increased $T_m$ values of these proteins. The effect of calcium binding on stability of serine protease, subtilisin S41 from the *Antarctic Bacillus*, also has been reported.

Improvements in stability also have been accomplished by chemical modification and immobilization. Chemical modification and immobilization have been used for improving protein stability by reducing conformational flexibility. For example, glycosidation of phenylalanine dehydrogenase with cyclodextrin derivatives enhanced its stability. Immobilization of penicillin G acylase on glyoxyl-agarose supports via lysine-mediated coupling improved its stability. In addition, reduced conformational flexibility can also be achieved by cross-linking the N- and C-termini of a target protein. For instance, beta lactamase and dihydrofolate reductase with their respective N- and C-termini connected through backbone cyclization were slightly more stable than the wild-type ones.

Previous methods of stabilizing proteins do have limitations. Enhanced stabilization achieved by rational, combinatorial and data-driven design involves changes in residues of a target protein usually in the form of mutations and recombinations. These changes very often compromise intrinsic properties of proteins, such as activity and specificity. This also occurs with chemical modification of proteins and their immobilization. Reduced conformational flexibility by modification and immobilization usually result in the significant loss of enzymatic activity. Recently, comprehensive directed evolution studies have demonstrated that stability and activity are not always inversely correlated. For instance, directed evolution of phosphate dehydrogenase led to identification of the variant with improved stability and activity. However, mutations and recombinations that improve stability with no compromise in activity or specificity are very rare and difficult to predict. This limitation would be even worse for stabilization of proteins with discontinuous catalytic domains. Mutation of residues to those commonly found in naturally existing stable counterparts improved stability of mesophilic proteins with no activity loss. However, only a small fraction of thermophilic proteins in nature have been identified. Also, a thermophilic protein with desired properties (such as activity and selectivity) is not always available from naturally existing ones. Employment of chaperones for stabilization is not very practical due to their lack of specificity and requirement of a relatively large dose. Stabilization by ligand addition requires tight binding (or the presence of excess ligands), which is not always available in normal proteins.

Therefore, it can be seen that new methods for the stabilization of proteins can be advantageous. It also can be seen that new methods for the stabilization of proteins that without modification of their primary sequence can be advantageous. The present invention is directed to such new methods and others.

BRIEF SUMMARY OF THE INVENTION

Insufficient stability of proteins is a fundamental problem that restricts their application in many areas. Although several strategies have been reported to improve protein stability, an approach that works for a specific protein may not always work for others. The conventional method for protein stabilization involves mutagenesis and therefore risks alteration of a protein's desired properties, such as activity and specificity.

The present invention is a novel and potentially general method for the stabilization of target protein domains without any modification of their primary sequence. The method of the present invention employs domain insertion of a target protein into a thermophilic scaffold protein. Insertion of a model target protein, exoinulinase (EI), into a loop of a thermophilic maltodextrin-binding protein from *Pyrococcus furiosus* (PfMBP) resulted in improvement of kinetic stability of the EI domain without any compromise in its activity.

It is anticipated that the described methodology for improving protein stability with little or no compromise in intrinsic properties will be directly relevant to a host of other systems, including enzymatic biodiesel/bioethanol production, enzymatic synthesis of organic/polymeric materials, immobilization of a protein on surfaces and employment of a protein for therapeutic purposes.

Limited stability is a common problem associated with most proteins. The results of the rational, combinatorial and data-driven design of highly stable proteins have revealed the presence of different ways for stabilization. This underscores the difficulty in developing a general strategy of enhancing the protein stability and the importance of individual structural contexts in the success of conventional stabilization methods. Enhanced stabilization achieved by these conventional methods involves changes in side chains of target protein residues usually in the form of mutations and recombinations. These changes very often compromise intrinsic properties of proteins. Usually mutations and recombinations that improve stability with no compromise in activity or specificity are very rare and difficult to predict. Mutation of residues to those commonly found in naturally existing stable counterparts improved stability of mesophilic proteins with no activity loss. However, only a small fraction of thermophilic proteins in nature have been identified and natural thermophilic proteins with desired activity and selectivity are not always available.

In order to improve stability of a protein with no change in side chains of its residues, we employ a thermophilic protein as a robust scaffold with which a target protein domain is fused. Two possible modes of connection exist, "end-to-end" or "insertional" fusion. In general, the end-to-end fusion of two distinct proteins, in which the N-terminus of one protein is connected to the C-terminus of the other, keeps the functions of both proteins unchanged. On the other hand, the insertional fusion, where one protein is inserted into the middle of the other, often produces functional "cross-talking" between the proteins. As insertion involves more than one connection, the resultant fusion protein is expected to form a more stable structure if an insertion site is properly selected.

For these reasons, we believe that some specific insertion modes of a target protein into a thermophilic protein could improve target protein-associated (thermo)stability. The insertional fusion can be readily achieved in both site-specific and random ways using recombinant DNA techniques.

A thermophilic maltose binding protein from *Pyrococcus furiosus* (PfMBP) was chosen as a stabilizing scaffold protein. Currently available 3D structural information on PfMBP is also useful for the selection of an insertion site. Insertion of the entire protein domain into another protein often results in generation of a nonfunctional protein complex and structural modeling to predict successful domain insertion sites is very challenging. Loop-forming residues 125-126 of PfMBP instead were selected as the initial insertion site as a loop region of a given protein is in general tolerant to modifications, such as mutations and insertions, among many other structural units.

Exoinulinase from *Bacillus* sp. Snu-7 (EI) was chosen as an initial model target protein. EI is a 450-residue glycoside hydrolase catalyzing release of the terminal fructose from the non-reducing end of inulin. We inserted the wild-type EI between residues 125 and 126 of PfMBP to create a protein complex named PfMBP-EI125 and measured its EI activity at 37° C. PfMBP-EI125 displayed nearly the same activity as the wild-type EI (the ratio of activity of the PfMBP-EI125 to the wild-type EI=0.96±0.04). Kinetic stabilities of the wild-type EI and PfMBP-EI125 were evaluated by measuring their respective activities over the time during incubation at 37° C. Interestingly, the kinetic stability at 37° C. of PfMBP-EI125 was much higher than that of the wild-type EI. The time-course activities of the wild-type EI followed a second-order inactivation ($R^2>0.94$). Consistent with the second-order inactivation kinetics, the formation of EI precipitate was observed after 20 day incubation of the wild-type EI. As a result, the concentration of EI in the solution was significantly reduced after a 20 day incubation. No precipitation was however observed in PfMBP-EI125 and its concentration in the solution remained the same after the 20 day incubation. The order of inactivation kinetics of PfMBP-EI125 could not be determined because no sufficient activity loss during the given incubation at 37° C. was observed. A similar decay was observed in circular dichorism and intrinsic tryptophan fluorescence of the wild-type EI and PfMBP-EI125, indicating that their secondary and tertiary structures changed at the same rate.

The connection between PfMBP and EI created by domain insertion should cause proximity of these two proteins, which may allow strong interactions between those. To test whether the proximity of protein domains created by domain insertion is required for stabilization, kinetic stability of the wild-type EI mixed with the purified PfMBP was evaluated. Coincubation with PfMBP yielded no significant improvement in kinetic stability of EI. The EI precipitate was also formed from the sample containing EI coincubated with PfMBP after 20 days at 37° C. These indicate that stabilization was achieved by the specific linkage between EI and PfMBP, not by non-specific effects caused by the presence of PfMBP. Whether the observed stabilization effect of domain insertion can be achieved by end-to-end connection, employed for construction of PfMBP-EI381, was examined. The end-to-end connection between PfMBP and EI within PfMBP-EI381 yielded a low initial activity (~35% of the wild-type EI) and no improvement of kinetic stability. The formation of EI precipitate was also observed after 20 day incubation of PfMBP-EI381 at 37° C. These data suggest that only insertional, not end-to-end, fusion improved kinetic stability of EI.

Herein, we show that domain insertion into PfMBP can significantly improve kinetic stability of EI. Unlike conventional stabilization methods, the approach described herein does not require any change on a target protein except for its connection to the scaffold protein. As a result, intrinsic properties of a target protein, such as activity and specificity, including enzymatic activity, can be largely maintained These features, and other features and advantages of the present invention will become more apparent to those of ordinary skill in the art when the following detailed description of the preferred embodiments is read in conjunction with the appended figures.

BRIEF DESCRIPTION OF THE FIGURES

FIG. 1: Amino acid sequences of PfMBP-EI125 and PfMBP-EI381. The numbers indicate the amino acid numbers of given proteins. The signal sequence of EcMBP was included for all protein complexes to enable export to the periplasm.

FIG. 2: Time-course changes in (a) exoinulinase activity, (b) ellipticity at 220 nm and (c) tryptophan fluorescence of the wild-type EI (□), PfMBP-EI125 (Δ), PfMBP-EI381 (◇), and an equimolar mixture of PfMBP+the wild-type EI (○) during incubation at 37° C. The protein concentration of the wild-type EI, PfMBP, PfMBP-EI125 and PfMBP-EI381 in the assay buffer was 1 μM. (a) Activity was measured using 500 μM of inulin. Activity of each protein sample at time zero was set to 100%. Activities of the wild-type EI, PfMBP-EI125 and PfMBP+the wild-type EI were all similar at the beginning of incubation. The errors represent one standard deviation (n≥3). (b) and (c), Ellipticity and tryptophan fluorescence at time zero was set to 100% for each protein sample. Excitation wavelength was 280 nm and emission was monitored at 337 nm.

FIG. 3: The amount of soluble proteins during incubation at 37° C. Protein samples were centrifuged after 0 and 20-day incubation at 37° C., and the supernatants were loaded in a SDS-PAGE gel. All samples contained 1 μM of proteins. M: molecular weight marker. 1: PfMBP-EI125 at the beginning of incubation. 2: PfMBP-EI125 after 20-day incubation. 3: the wild-type EI at the beginning of incubation. 4: the wild-type EI after 20-day incubation. *: PfMBP-EI125. **: the wild-type EI.

DETAILED DESCRIPTION OF PREFERRED EMBODIMENTS

Limited stability is a common problem associated with many proteins. The results of rational, combinatorial and data-driven design of highly stable proteins have revealed different paths for stabilization. This underscores the difficulty in developing a general strategy for enhancing protein stability and the importance of individual structural contexts in the success of conventional stabilization methods. Enhanced stabilization achieved by these conventional methods involves changes in side chains of target protein residues usually in the form of point mutations. These changes very often compromise a protein's intrinsic properties. Rational and directed evolution approaches can sometimes result in identification of protein variants with improved stability without compromised activity. However, mutations that improve stability with no compromise in activity or specificity are in general very rare and difficult to predict, especially for a large protein with multiple discontinuous catalytic domains. Furthermore, such mutation-based methods must be optimized for every specific target, as there are no general rules for protein stabilization. Mutation of residues to those commonly found in naturally existing thermostable counterparts can improve stability of mesophilic proteins without activity loss. However, only a small fraction of thermophilic proteins in nature have been identified and natural thermophilic proteins with desired activity and selectivity are not always available.

In order to improve the stability of a protein without changing its primary sequence, a thermophilic protein is employed as a robust scaffold to which a target protein domain is fused. Two possible modes of connection exist, "end-to-end" and "insertional" fusion. In end-to-end fusion, the N-terminus of one protein is connected to the C-terminus of the other. Unlike end-to-end fusion, insertional fusion, in which one protein is inserted into the middle of the other, often produces functional "cross-talk" between the proteins. As insertion involves more than one connection, the resultant fusion protein has the potential to form a more stable structure if an insertion site is properly selected. For these reasons, it is speculated that some specific insertion modes of a target protein into a thermophilic protein could improve target protein-associated stability. Insertional fusion can be readily achieved by site-specific and random methodologies using recombinant DNA techniques. The close proximity of the N- and C-termini of an inserted protein seems to increase the chance of successful insertion. Nearly 50% of single-domain proteins have their N- and C-termini proximal, indicating the potential application of the present method to a wide range of proteins. The incorporation of appropriate linkers between the protein domains can assist in achieving functional insertion and help accommodate insertion of proteins whose two termini are more distal.

A maltodextrin-binding protein from the hyper-thermophile *Pyrococcus furiosus* (PfMBP) is a 43 kDa periplasmic protein and highly stable against heat and chemical denaturation. For instance, PfMBP displays little loss in a secondary structure at 85° C. or in 6M guanidine hydrochloride whereas the mesophilic maltodextrin-binding protein from *Escherichia coli* (EcMBP) unfolds at 65° C. or in 1M guanidine hydrochloride. PfMBP was chosen as the stabilizing scaffold protein for several reasons. First, end-to-end fusion to maltodextrin-binding proteins from bacteria and archaea often stabilizes the fusion partner by increasing its solubility and preventing the formation of inclusion bodies. The thermophilic nature of PfMBP might allow exploring the insertion sites, which would be unavailable in a mesophilic protein due to limited stability. Second, 3D structural information on PfMBP is available. The loop-forming residues 125 and 126 of PfMBP were selected as the initial insertion site (FIG. 1), as surface loops are in general more tolerant to mutations and insertions than other structural units. The known amino acid sequence of PfMBP is (SEQ ID NO: 1)

```
MKIKTGARILALSALTTMMFSASALAKIEEGKVVIWHAMQPNELEVFQSL

AEEYMALCPEVEIVFEQKPNLEDALKAAIPTGQGPDLFIWAHDWIGKFAE

AGLLEPIDEYVTEDLLNEFAPMAQDAMQYKGHYYALPFAAETVAIIYNKE

MVSEPPKTFDEMKAIMEKYYDPANEKYGIAWPINAYFISAIAQAFGGYYF

DDKTEQPGLDKPETIEGFKFFFTEIWPYMAPTGDYNTQQSIFLEGRAPMM

VNGPWSINDVKKAGINFGVVPLPPIIKDGKEYWPRPYGGVKLIYFAAGIK

NKDAAWKFAKWLTTSEESIKTLALELGYIPVLTKVLDDPEIKNDPVIYGF
```

-continued

GQAVQHAYLMPKSPKMSAVWGGVDGAINEILQDPQNADIEGILKKYQQEI

LNNMQGHHHHHH;

and the known DNA sequence coding for PfMBP is (SEQ ID NO: 2)
atgaaaataaaaacaggtgcacgcatcctcgcattatccgcattaacgac gatgatgttttccgcctcggctctcgccaaaatcgaagaaggaaaagttg ttatttggcatgcaatgcaacccaatgagcttgaggtcttccaaagctta gcggaagaatacatggcactctgtccagaagttgagatagttttttgaaca aaagccaaacttggaagatgctcttaaggctgcaatacccacaggtcaag gtcctgacctctttatctgggctcacgactggattggaaagtttgctgag gcaggattacttgagccaattgatgaatatgtaactgaagatctccttaa cgagtttgctccaatggcccaggatgcaatgcagtataaaggtcactact atgctctaccattcgccgctgaaacagttgcaataatctacaacaaagaa atggttagcgagccaccgaaacctttgatgagatgaaggcaataatgga gaagtactatgatccagcaaatgagaagtatggaatagcttggccaatta atgcctactttatctcagcaattgctcaggcctttggtggttactacttt gacgacaaaacagagcaaccgggactagataagcctgagacaatcgaagg atttaagttcttcttcacagaaatatggccatacatggctccaactggag actacaacactcaacagagtatattcctcgagggtagagccccaatgatg gttaatggtccatggagcattaacgacgttaagaaggcaggaataaaactt tggagtggttccactacctccaataatcaaggatggtaaggagtactggc caaggccttacggtggagttaagttgatttacttcgcagcgggaataaag aacaaggatgctgcatggaagttcgcaaagtggcttaccacaagcgaaga gtcaattaagacattggcactagagctgggatacataccggttcttacga aggttcttgatgatccagaaattaagaatgatccagtaatctatggctt ggacaagcagttcagcacgcatacctaatgccaaagagtccaaagatgag tgctgtttggggcggagttgatgggcaattaacgaaatcctccaagatc cacaaaacgctgacattgaaggaatactaaagaagtatcaacaagaaatc cttaacaacatgcaaggccatcatcaccaccatcactgataa.

The residues 125 and 126 of PfMBP are glutamic acid and methionine, respectively, when numbered according to known numbering methods such as Evdokimov, A. G., Anderson, D. E., Routzahn, K. M. and Waugh, D. S.; J. Mol. Biol., 305, 891-904 (2001).

Figure 2:
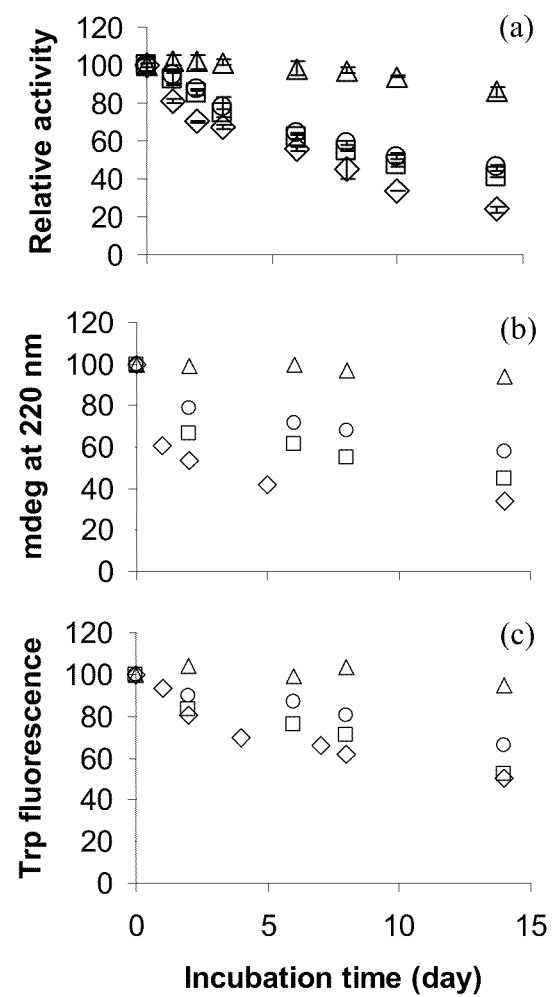
Figure 3:
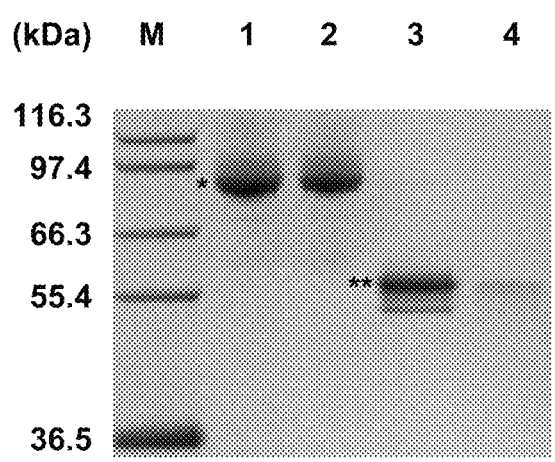

Exoinulinase from *Bacillus* sp. Snu-7 (EI) was chosen as an initial model target protein as it has limited stability at 37° C. EI is a 495-residue glycoside hydrolase catalyzing release of the terminal fructose from the non-reducing end of inulin. Wild-type EI lost activity irreversibly during incubation at 37° C. (FIG. 2a). The time-course activities of the wild-type EI followed a second-order inactivation ($R^2$>0.94). Consistent with the second-order inactivation kinetics, the formation of precipitate was observed after a 20-day incubation of the wild-type EI (data not shown). As a result, the concentration of soluble EI was significantly reduced after the 20-day incubation (FIG. 3).

The wild-type EI was inserted between residues 125 and 126 of PfMBP to create a protein complex named PfMBP-EI125 (FIG. 1-*top*) and measured its exoinulinase activity at 37° C. PfMBP-EI125 displayed nearly the same activity as the wild-type EI. The ratio of activity of PfMBP-EI125 to wild-type EI was 0.96±0.04. Kinetic stability of PfMBP-EI125 was evaluated by measuring their respective activities, particularly its enzymatic activities, as a function of time during incubation at 37° C. As desired, the kinetic stability of PfMBP-EI125 was much higher than that of the wild-type EI (FIG. 2a). No precipitation was observed in solutions of PfMBP-EI125 (data not shown) and its concentration in solution remained unchanged after a 20-day incubation at 37° C. (FIG. 3). The order of inactivation kinetics of PfMBP-EI125 could not be determined due to minimal activity loss during incubation. The decay in both proteins' circular dichroism and intrinsic tryptophan fluorescence spectra mirrored the loss in activity (FIGS. 2b and c), suggesting that changes in secondary and tertiary structures were responsible for the loss in activity.

To test whether fusion of the protein domains was required for stabilization, the kinetic stability of an equimolar mixture of wild-type EI and PfMBP was evaluated. Coincubation with PfMBP at an equimolar ratio yielded no significant improvement in the kinetic stability of wild-type EI (FIG. 2) and did not prevent the precipitation observed after 20 days (data not shown). This indicates that stabilization was achieved by the linkage between EI and PfMBP, not by non-specific effects caused by the presence of PfMBP. Whether the observed stabilization effect of domain insertion could be achieved by end-to-end fusion was next examined. The end-to-end fusion between PfMBP and EI domains within PfMBP-EI381 (FIG. 1-*bottom*) resulted in reduced initial activity (~35% of the wild-type EI) and no improvement of kinetic stability (FIG. 2). The formation of precipitate was also observed after a 20-day incubation of PfMBP-EI381 at 37° C. (data not shown). Thus, simple end-to-end fusion was not sufficient to improve the kinetic stability of EI, implying there is something special about the insertional fusion. This may include specific relative orientations of EI and PfMBP domains in the insertional fusion that favor inter-domain interactions stabilizing the inserted protein, and/or the presence of two "tethers" between the domains in the insertional fusion. The result also suggests that the improved stability of the EI domain achieved by insertional fusion was not merely due to enhancement of solubility upon fusion to PfMBP, which has been known to prevent inclusion body formation of end-to-end fusion partners.

A comparison of results of the present method with that of previous insertion studies into EcMBP suggests that a thermophilic scaffold domain is required for the inserted domain to acquire improved stability. The structures of PfMBP and EcMBP closely superimpose and residues 120 and 121 of EcMBP are structurally aligned with residues 125 and 126 of PfMBP. Insertion of the wild-type beta-lactamase into EcMBP between residues 120 and 121 resulted in the formation of inclusion bodies in previous studies. The formation of inclusion bodies was also observed in insertion of a short 13-aa peptide sequence into EcMBP at the same site. This suggests that inclusion body formation could primarily be due to incomplete folding of EcMBP, and the high stability displayed by PfMBP might allow for insertion into the sequence space, which is not available in the moderately stable EcMBP. Overall, the nature of a scaffold protein may determine folding and intracellular stability of a protein insertion complex.

In the present invention, it has been found that domain insertion of EI into PfMBP can significantly improve their stability of EI. Unlike conventional stabilization methods, the approach described here does not require any change on a target protein except for its connection to the scaffold protein. As a result, the intrinsic properties of a target protein, such as activity and specificity, particularly enzymatic activity, can be largely maintained.

Materials and Methods

Reagents

Oligonucleotides were purchased from Operon Biotechnologies Inc. (Huntsville, Ala., USA). High fidelity platinum pfx DNA polymerase and Electromax DH5α-E cells were purchased from Invitrogen (Carlsbad, Calif., USA). All DNA purification kits were purchased from Qiagen (Valencia, Calif., USA). His-tag protein purification kits and columns were purchased from Novagen (Madison, Wis., USA) and GE healthcare (Buckinghamshire, England, UK), respectively. Restriction enzymes and T4 DNA ligase were purchased from New England Biolabs, Inc. (Ipswich, Mass., USA). Inulin, all other antibiotics and biological reagents were purchased from Thermo Fisher Scientific (Waltham, Mass., USA).

DNA Construction

The plasmid, pREX12, for expression of the wild-type exoinulinase (EI) was kindly provided by Dr. S. I. Kim (Seoul National University, Seoul, Korea). PCR was used for replicating DNA sequences coding for the entire maltodextrin-binding protein from *Pyrococcus furiosus* (PfMBP) from plasmid FLIPmal_Pf generously provided by Dr. W. B. Frommer (Carnegie Institute of Plant Biology, Stanford, Calif., USA). A six histidine tag was genetically attached to the C-termini of PfMBP, for protein purification. The signal sequence of maltodextrin-binding protein from *Escherichia coli* (EcMBP) (residue 1-30) was added to PfMBP for export of the protein to the periplasm of *E. coli*. Sequences of PfMBP and EcMBP were aligned beginning with the sixth residue of PfMBP (numbered according to Evdokimov et al.). The desired PCR products were purified by QIAquick PCR purification and QIAquick gel extraction kits.

For construction of PfMBP-EI125 and PfMBP-EI381, DNA sequences coding for the wild-type EI, and parts of PfMBP were amplified by PCR from pREX12 and FLIPmal_pf, respectively. The purified DNA fragments were assembled into a full gene by overlap extension PCR. A six histidine tag was genetically added to the C-terminus of each fusion complex. The signal sequence of EcMBP was included in PfMBP-EI125 and PfMBP-EI381. No additional linker was added between protein domains.

The DNA sequences coding for PfMBP, PfMBP-EI125 and PfMBP-EI381 were digested by BamHI and SpeI restriction enzymes to create sticky ends needed for ligation. Plasmid pDIM-C8-MalE was digested with BamHI and SpeI restriction enzymes, and purified by QIAquick gel extraction kit. The digested inserts and plasmids were then ligated using T4 ligase and supplied buffer. Ligation products were then electroporated into 40 µl Electromax DH5α-E using a Bio-Rad Gene Pulser (Hercules, Calif., USA). Electroporated cells were subsequently incubated for 1 hour at 250 rpm and 37° C. in a New Brunswick Scientific Innova TM4230 incubator (Edison, N.J., USA). Electroporated cells were then plated on LB agar plate supplemented with 50 µg/ml chloramphenicol and incubated for 16-24 hours at 37° C. in the incubator. The colonies growing on LB agar plate supplemented with 50 µg/ml chloramphenicol were picked and recultured in test tubes containing 10 ml LB media and 50 µg/ml chloramphenicol. Plasmid DNA was extracted from recultured colonies using QIAprep spin miniprep kit according to the manufacturer's protocol. The extracted DNA was then sequenced at Geneweiz, Inc. (South Plainfield, N.J., USA).

Protein Expression and Purification

One liter of LB media containing 50 µg/ml chloramphenicol was inoculated with 2% overnight culture and shaken at 250 rpm at 37° C. Cells expressing the wild-type EI, PfMBP, PfMBP-EI125 and PfMBP-EI381 were grown at 37° C. until the optical density at 600 nm was 0.6. Expression of the wild-type EI, PfMBP, PfMBP-EI125 and PfMBP-EI381 was then induced by adding 1 mM isopropyl-beta-D-1-galactopyranoside (IPTG). After induction, the cell culture was shaken at 250 rpm for another 16-24 hours at 23 or 30° C. Cells were pelleted by centrifuging at 5000 rpm at 4° C. for 20 minutes using a Beckman Coulter Avanti JE centrifuge (Fullerton, Calif., USA). The pelleted cells were then stored at −75° C. until ready for use. For protein purification, the pelleted cells were resuspended in 0.05 M Tris-HCl buffer containing 0.5 M NaCl, pH 7.5 with a dilution ratio of approximately 10 ml per gram of cells. The cells were then lysed by French Press purchased from Thermo Fisher Scientific and the cell lysates were centrifuged at 20,000 rpm at 4° C. Supernatants containing the soluble proteins were then recovered and passed over the $Ni^{2+}$ column. Bound proteins were eluted with imidazole solution and dialyzed at 4° C. against at least fifteen liter of 0.05 M Tris-HCl buffer, pH 7.5. Purified protein samples were stored at 4° C.

The purities of the proteins were estimated by Coomassie Blue staining of sodium dodecyl sulfate polyacrylamide gel electrophoresis (SDS-PAGE) and were greater than 95%. Protein concentrations were determined using extinction coefficients at 280 nm as calculated according to Gill and von Hippel or the Bradford assay.

Enzyme Assay

Hydrolysis of inulin by the wild-type EI, an equimolar mixture of PfMBP+the wild-type EI, PfMBP-EI125 and PfMBP-EI381 was measured in 0.05 M Tris-HCl buffer, pH 7.5 at 37° C., as described previously. The protein concentration of the wild-type EI, PfMBP, PfMBP-EI125 and PfMBP-EI381 in the assay buffer was 1 µM. Protein samples were incubated at 37° C. prior to addition of inulin. The final concentration of inulin was 500 µM in all assays. For the measurement of inulin hydrolysis, a reaction mixture containing a protein and inulin was incubated at 37° C. for additional one hour followed by addition of 3,5-dinitosalicylic acid. The reaction mixture was then boiled for 10 min and an amount of liberated reducing sugar was determined by absorbance at 550 nm as previously described.

In order to monitor irreversible inactivation of proteins over time, protein samples were withdrawn at different time points of incubation and their enzymatic hydrolyses were measured at the incubation temperature.

The second-order irreversible inactivation kinetics was able to capture the activity loss over time of the wild-type EI, PfMBP-EI381 and an equimolar mixture of PfMBP+the wild-type EI ($R^2>0.94$), but not PfMBP-EI125. This is because PfMBP-EI125 did not display sufficient activity loss during the given incubation time period at 37° C. Therefore, no further attempt to determine the irreversible inactivation constants of exoinulinase activity was made.

Circular Dichroism Spectroscopy

Secondary structures of proteins were determined using circular dichroism (CD), collected using a Jasco J-815 circular spectrometer (Easton, Md., USA) in the far-UV range with a 0.1 cm pathlength of cuvette. The protein samples were withdrawn at several time points during incubation at 37° C. Ellipticity of samples containing 1 µM of the wild-type EI in the presence and absence of equimolar PfMBP at each wavelength was measured without dilution at 37° C. Ellipticity of samples containing 1 µM of PfMBP-EI125 and PfMBP-EI381 was measured in the same way. The spectrum of the background (buffer only) was measured and then subtracted from the sample spectrum.

Intrinsic Tryptophan Fluorescence

Intrinsic tryptophan fluorescence of protein samples was measured using a Photon Technology QuantaMaster QM-4 spectrofluorometer (Birmingham, N.J., USA). Excitation wavelength was 280 nm and emission was monitored at 337 nm. The protein samples were withdrawn at several time points during incubation at 37° C. Intrinsic tryptophan fluorescence of samples containing 1 µM of the wild-type EI with and without addition of equimolar PfMBP was measured without dilution. Intrinsic tryptophan fluorescence of samples containing 1 µM of PfMBP-EI125 and PfMBP-EI381 was measured in the same way. The spectrum of the background (buffer only) was measured and then subtracted from the sample spectrum.

SDS-PAGE for Determination of the Amount of Soluble Proteins

Protein samples were incubated for the designated time period and then centrifuged. The supernatant of each sample was loaded in the SDS-PAGE gel. The gel was then stained with Coomassie Blue.

Thus, using the above disclosed illustrative materials and methods, it has been found that domain insertion of EI into PfMBP can significantly improve its kinetic stability. Unlike conventional stabilization methods, the approach described herein does not require any change on a target protein except for its connection to the scaffold protein. As a result, the intrinsic properties of a target protein, such as activity and specificity, can be largely maintained.

It is to be understood that the present invention is by no means limited to the particular constructions and method steps herein disclosed or shown in the drawings, but also comprises any modifications or equivalents within the scope of the claims known in the art. It will be appreciated by those skilled in the art that the devices and methods herein disclosed will find utility with respect to enzymatic reactions employed in the biochemical industry and with therapeutic proteins.

REFERENCES

A1. Eijsink, V. G., Bjork, A., Gaseidnes, S., Sirevag, R., Synstad, B., van den Burg, B. & Vriend, G. (2004) Rational engineering of enzyme stability. *J. Biotechnol.* 113, 105-20.

A2. Eijsink, V. G., Gaseidnes, S., Borchert, T. V. & van den Burg, B. (2005) Directed evolution of enzyme stability. *Biomol. Eng.* 22, 21-30.

A3. Bommarius, A. S., Broering, J. M., Chaparro-Riggers, J. F. & Polizzi, K. M. (2006) High-throughput screening for enhanced protein stability. *Curr. Opin. Biotechnol.* 17, 606-610.

A4. Korkegian, A., Black, M. E., Baker, D. & Stoddard, B. L. (2005) Computational thermostabilization of an enzyme. *Science* 308, 857-860.

A5. Johannes, T. W., Woodyer, R. D. & Zhao, H. M. (2005) Directed evolution of a thermostable phosphite dehydrogenase for NAD(P)H regeneration. *Appl. Environ. Microbiol.* 71, 5728-5734.

A6. Giver, L., Gershenson, A., Freskgard, P. O. & Arnold F. H. (1998) Directed evolution of a thermostable esterase *Proc. Natl. Acad. Sci. USA*. 95, 12809-12813.

A7. Lehmann, M. & Wyss, M. (2001) Engineering proteins for thermostability: the use of sequence alignments versus rational design and directed evolution. *Curr. Opin. Biotechnol.* 12, 371-375.

A8. Doi, N. & Yanagawa, H. (1999) Insertional gene fusion technology. *FEBS Lett.* 457, 1-4.

A9. Ostermeier, M. (2005) Engineering allosteric protein switches by domain insertion. *Protein Eng. Des. Sel.* 18, 359-364.

A10. Krishna, M. M. & Englander, S. W. (2005) The N-terminal to C-terminal motif in protein folding and function. *Proc. Natl. Acad. Sci. USA*. 102, 1053-1058.

A11. Evdokimov, A. G., Anderson, D. E., Routzahn, K. M. & Waugh, D. S. (2001) Structural basis for oligosaccharide recognition by *Pyrococcus furiosus* maltodextrin-binding protein. *J. Mol. Biol.* 305, 891-904.

A12. Gardner, K. H., Zhang, X., Gehring, K. & Kay, L. (1998) Solution NMR studies of a 42-kDa *Escherichia coli* maltose binding protein/β-cyclodextrin complex: chemical shift assignments and analysis. *J. Am. Chem. Soc.* 120, 11738-11748.

A13. Fox, J. D., Routzahn, K. M., Bucher, M. H. & Waugh, D. S. (2003) Maltodextrin-binding proteins from diverse bacteria and archaea are potent solubility enhancers. *FEBS Lett.* 537, 53-57.

A14. Bloom, J. D., Labthavikul, S. T., Otey, C. R. & Arnold, F. H. (2006) Protein stability promotes evolvability. *Proc. Natl. Acad. Sci. USA*. 103, 5869-5874.

A15. Puziss, J. W., Harvey, R. J. & Bassford, P. J. Jr. (1992) Alterations in the hydrophilic segment of the maltose-binding protein (MBP) signal peptide that affect either export or translation of MBP. *J. Bacteriol.* 174, 6488-6497.

A16. Kim, K.-Y., Koo, B.-S., Jo, D. & Kim. S.-I. (2004) Cloning, expression, and purification of exoinulinase from *Bacillus* sp. Snu7. *J. Microbiol. Biotechnol.* 14, 344-349.

A17. Betton, J. M., Jacob, J. P., Hofnung, M. & Broome-Smith, J. K. (1997) Creating a bifunctional protein by insertion of beta-lactamase into the maltodextrin-binding protein. *Nat. Biotechnol.* 15, 1276-1279.

A18. Martineau, P., Leclerc, C. & Hofnung, M. (1996) Modulating the immunological properties of a linear B-cell epitope by insertion into permissive sites of the MalE protein. *Mol. Immunol.* 33, 1345-1358.

B1. Kim, K.-Y., Koo, B.-S., Jo, D. & Kim. S.-I. (2004) Cloning, expression, and purification of exoinulinase from *Bacillus* sp. Snu7. *J. Microbiol. Biotechnol.* 14, 344-349.

B2. Puziss, J. W., Harvey, R. J. & Bassford, P. J. Jr. (1992) Alterations in the hydrophilic segment of the maltose-binding protein (MBP) signal peptide that affect either export or translation of MBP. *J. Bacteriol.* 174, 6488-6497.

B3. Evdokimov, A. G., Anderson, D. E., Routzahn, K. M. & Waugh, D. S. (2001) Structural basis for oligosaccharide recognition by *Pyrococcus furiosus* maltodextrin-binding protein. *J. Mol. Biol.* 305, 891-904.

B4. Kim, J. R. & Ostermeier, M. (2006) Modulation of effector affinity by hinge region mutations also modulates switching activity in an engineered allosteric TEM1 beta-lactamase switch. *Arch. Biochem. Biophys.* 446, 44-51.

B5. Gill, S. C. & von Hippel, P. H. (1989) Calculation of protein extinction coefficients from amino acid sequence data. *Anal. Biochem.* 182, 319-326.

B6. Bradford, M. M. (1976) A Rapid and Sensitive Method for the Quantitation of Microgram Quantities of Protein Utilizing the Principle of Protein-Dye Binding. *Anal. Biochem.* 72, 248-254.

B7. Melius, P. (1971) Isolation of yeast invertase by sephadex gel chromatography. A biochemistry laboratory experiment. *J. Chem. Edu.* 48, 765-766.

B8. McManus-Munoz, S. & Crowder, M. W. (1999) Kinetic mechanism of metallo-beta-lactamase L1 from *Stenotrophomonas maltophilia*. *Biochemistry* 38, 1547-1553.

B9. Sigal, I. S., DeGrado, W. F., Thomas, B. J. & Petteway, S. R., Jr. (1984) Purification and properties of thiol beta-lactamase. A mutant of pBR322 beta-lactamase in which the active site serine has been replaced with cysteine. *J. Biol. Chem.* 259, 5327-5332.

B10. Kumar, S., Adediran, S. A., Nukaga, M. & Pratt R F. (2004) Kinetics of turnover of cefotaxime by the *Enterobacter cloacae* P99 and GCI beta-lactamases: two free enzyme forms of the P99 beta-lactamase detected by a combination of pre- and post-steady state kinetics. *Biochemistry* 43, 2664-2072.

B11. Sowek, J. A., Singer, S. B., Ohringer, S., Malley, M. F., Dougherty, T. J., Gougoutas, J. Z. & Bush, K. (1991) Substitution of lysine at position 104 or 240 of TEM-1pTZ18R beta lactamase enhances the effect of serine-164 substitution on hydrolysis or affinity for cephalosporins and the monobactam aztreonam. *Biochemistry* 30, 3179-3188.

C1. Gübitz, G. M. and Paulo, A. C. (2003) New substrates for reliable enzymes: enzymatic modification of polymers. *Curr. Opin. Biotechnol.* 14, 577-582.

C2. Jaeger, K. E. and Eggert, T. (2002) Lipases for Biotechnology. *Curr. Opin. Biotechnol.* 13, 390-397.

C3. Kobayashi, S. and Uyama, H. (2002) In vitro polyester synthesis via enzymatic polymerization. *Curr. Org. Chem.* 6, 209-222.

C4. Daniel, R. M., Cowan, D. A., Curran, M. and Morgan, H. W. (1982) A correlation between protein thermostability and susceptibility to proteolysis. *Biochem. J.* 207, 641-644.

C5. Owusu, R. K. and Cowan, D. A. (1989) A correlation between microbial protein thermostability and resistance to denaturation in aqueous-organic solvent two-phase systems. *Enz. Microb. Technol.* 11, 568-574.

C6. Cowan, D. A. (1997) Thermophilic proteins: stability and function in aqueous and organic solvents. *Comp. Biochem. Physiol. A Physiol.* 118, 429-438.

C7. Eijsink, V. G., Bjork, A., Gaseidnes, S., Sirevag, R., Synstad, B., van den Burg, B. and Vriend, G. (2004) Rational engineering of enzyme stability. *J. Biotechnol.* 113, 105-20.

C8. Van den Burg, B., Vriend, G., Veltman, O. R., Venema, G. and Eijsink, V. G. (1998) Engineering an enzyme to resist boiling. *Proc. Natl. Acad. Sci. USA.* 95, 2056-2060.

C9. Hasegawa, J., Shimahara, H., Mizutani, M., Uchiyama, S., Arai, H., Ishii, M., Kobayashi, Y., Ferguson, S. J., Sambongi, Y. and Igarashi, Y. (1999) Stabilization of *Pseudomonas aeruginosa* cytochrome c551 by systematic amino acid substitutions based on the structure of thermophilic *Hydrogenobacter thermophilus* cytochrome c552. *J. Biol. Chem.* 274, 37533-37537.

C10. Adams, M. W. and Kelly, R. M. (1998) Finding and using hyperthermophilic enzymes. *Trends Biotechnol.* 16, 329-332.

C11. Li, W. F., Zhou, X. X. and Lu, P. (2005) Structural features of thermozymes. *Biotechnol. Adv.* 23, 271-281.

C12. Renugopalakrishnan, V., Garduno-Juarez, R., Narasimhan, G., Verma, C. S., Wei, X. and Li, P. (2005) Rational design of thermally stable proteins: relevance to bionanotechnology. *J. Nanosci. Nanotechnol.* 5, 1759-67.

C13. Magliery, T. J. and Regan, L. (2004) Combinatorial approaches to protein stability and structure. *Eur. J. Biochem.* 271, 1595-1608.

C14. Eijsink, V. G., Gaseidnes, S., Borchert, T. V. and van den Burg, B. (2005) Directed evolution of enzyme stability. *Biomol. Eng.* 22, 21-30.

C15. Lehmann, M., Loch, C., Middendorf, A., Studer, D., Lassen, S. F., Pasamontes, L., van Loon, A. P. and Wyss, M. (2002) The consensus concept for thermostability engineering of proteins: further proof of concept. *Protein Eng.* 15, 403-411.

C16. Amin, N., Liu, A. D., Ramer, S., Aehle, W., Meijer, D., Metin, M., Wong, S., Gualfetti, P. and Schellenberger, V. (2004) Construction of stabilized proteins by combinatorial consensus mutagenesis. *Protein Eng. Des. Sel.* 17, 787-793.

C17. Polizzi, K. M., Chaparro-Riggers, J. F., Vazquez-Figueroa, E. and Bommarius, A. S. (2006) Structure-guided consensus approach to create a more thermostable penicillin G acylase. *Biotechnol. J.* 1, 531-536.

C18. Bommarius, A. S., Broering, J. M., Chaparro-Riggers, J. F. and Polizzi, K. M. (2006) High-throughput screening for enhanced protein stability. *Curr. Opin. Biotechnol.* 17, 606-610.

C19. Schlieker, C., Bukau, B. and Mogk, A. (2002) Prevention and reversion of protein aggregation by molecular chaperones in the *E. coli* cytosol: implications for their applicability in biotechnology. *J. Biotechnol.* 96, 13-21.

C20. Baneyx, F. and Mujacic, M. (2004) Recombinant protein folding and misfolding in *Escherichia coli*. Nat. Biotechnol. 22, 1399-1408.

C21. Kohda, K., Tsuji, Y., Takagi, M. and Imanaka, T. (1996) Cloning and functional-analysis of molecular chaperone genes from *Bacillus stearothermophilus* Sic1. *Biotechnol. Lett.* 18, 1061-1066.

C22. Muchowski, P. J. and Clark, J. I. (1998) ATP-enhanced molecular chaperone functions of the small heat shock protein human αB-crystallin. *Proc. Natl. Acad. Sci. USA* 95, 1004-1009.

C23. Yutani, K., Ogasahara, K., Tsujita, T. and Sugino, Y. (1987) Dependence of conformational stability on hydrophobicity of the amino acid residue in a series of variant proteins substituted at a unique position of tryptophan synthase alpha subunit. *Proc. Natl. Acad. Sci. USA* 84, 4441-4444.

C24. Millard, C. B., Shnyrov, V. L., Newstead, S., Shin, I., Roth, E., Silman, I. and Weiner, L. (2003) Stabilization of a metastable state of *Torpedo californica* acetylcholinesterase by chemical chaperones. *Protein Sci.* 12, 2337-2347.

C25. González, M., Bagatolli, L., Echabe, I., Arrondo, J., Argaraña, C., Cantor, C. and Fidelio, G. (1997) Interaction of biotin with streptavidin. *J. Biol. Chem.* 272, 11288-11294.

C26. González, M., Argaraña, C. and Fidelio, G. (1999) Extremely high thermal stability of streptavidin and avidin upon biotin binding. *Biomol. Eng.* 16, 67-72.

C27. Celej, M., Montich, G. and Fidelio, G. (2003) Protein stability induced by ligand binding correlates with changes in protein flexibility. *Protein Sci.* 12, 1496-1506.

C28. Miyazaki, K., Wintrode, P. L., Grayling, R. A., Rubingh, D. N. and Arnold, F. H. (2000) Directed evolution study of temperature adaptation in a psychrophilic enzyme. *J. Mol. Biol.* 297, 1015-1026.

C29. Polizzi, K. M., Bommarius, A. S., Broering, J. M. and Chaparro-Riggers, J. F. (2007) Stability of biocatalysts. *Curr. Opin. Chem. Biol.* 11, 220-225.

C30. Villalonga, R., Tachibana, S., Cao, R., Ramirez, H. L. and Asano, Y. (2006) Supramolecular-mediated thermostabilization of phenylalanine dehydrogenase modified with beta-cyclodextrin derivatives. *Biochem. Eng. J.* 30, 26-32.

C31. Villalonga, R., Tachibanab, S., Caoc, R., Matosa, M. and Asanob, Y. (2007) Glycosidation of phenylalanine dehydrogenase with O-carboxymethyl-poly-beta-cyclodextrin. *Enzyme Microb. Technol.* 40, 471-475.

C32. Abian, O., Grazu, V., Hermoso, J., Gonzalez, R., Garcia, J. L., Fernandez-Lafuente, R. and Guisan, J. M. (2004) Stabilization of penicillin G acylase from *Escherichia coli*: site-directed mutagenesis of the protein surface to increase multipoint covalent attachment. *Appl. Environ. Microbiol.* 70, 1249-1251.

C33. Iwai, H. and Plückthun, A. (1999) Circular beta-lactamase: stability enhancement by cyclizing the backbone. *FEBS Lett.* 459, 166-172.

C34. Scott, C. P., Abel-Santos, E., Wall, M., Wahnon, D. C. and Benkovic, S. J. (1999) Production of cyclic peptides and proteins in vivo. *Proc. Natl. Acad. Sci. USA.* 96, 13638-13643.

C35. Giver, L., Gershenson, A., Freskgard, P. O. and Arnold F. H. (1998) Directed evolution of a thermostable esterase *Proc. Natl. Acad. Sci. USA.* 95, 12809-12813.

C36. Zhang, N. Y., Suen, W. C., Windsor, W., Xiao, L., Madison, V. and Zaks, A. (2003) Improving tolerance of *Candida antarctica* lipase B towards irreversible thermal inactivation through directed evolution. *Protein Eng.* 16, 599-605.

C37. Hamamatsu, N., Nomiya, Y., Aita, T., Nakajima, M., Husimi, Y. and Shibanaka Y. (2006) Directed evolution by accumulating tailored mutations: thermostabilization of lactate oxidase with less trade-off with catalytic activity. *Protein Eng. Des. Sel.* 19, 483-489.

C38. Johannes, T. W., Woodyer, R. D. and Zhao, H. (2005) Directed evolution of a thermostable phosphite dehydrogenase for NAD(P)H regeneration. *Appl. Environ. Microbiol.* 71, 5728-5734.

C39. Jones, S., Stewart, M., Michie, A., Swindells, M. B., Orengo, C. and Thornton, J. M. (1998) Domain assignment for protein structures using a consensus approach: characterization and analysis. *Protein Sci.* 7, 233-242.

C40. Lehmann, M., Kostrewa, D., Wyss, M., Brugger, R., D'Arcy, A., Pasamontes, L. and van Loon, A. P. (2000) From DNA sequences to improved functionality: using protein sequence comparisons to rapidly design a thermostable consensus phytase. *Protein Eng.* 13, 49-57.

C41. Lehmann, M., Wyss, M. (2001) Engineering proteins for thermostability: the use of sequence alignments versus rational design and directed evolution. *Curr. Opin. Biotechnol.* 12, 371-375.

C42. Danson, M. J. and Hough, D. W. (1998) Structure, function and stability of enzymes from the Archaea. *Trends Microbiol.* 6, 307-314.

C43. Landenstein, R. and Antranikian, G. (1998) Proteins from hyperthermophiles: stability and enzymatic catalysis close to the boiling point of water. *Adv. Biochem. Eng. Biotechnol.* 61, 37-85.

C44. Vieille, C. and Zeikus, G. J. (2001) Hyperthermophilic enzymes: sources, uses, and molecular mechanisms for thermostability. *Microbiol. Mol. Biol. Rev.* 65, 1-43

C45. Doi, N. and Yanagawa, H. (1999) Insertional gene fusion technology. *FEBS Lett.* 457, 1-4.

C46. Ostermeier, M. (2005) Engineering allosteric protein switches by domain insertion. *Protein Eng. Des. Sel.* 18, 359-364.

C47. Guntas, G. and Ostermeier, M. (2004) Creation of an allosteric enzyme by domain insertion. *J. Mol. Biol.* 336, 263-273.

C48. Evdokimov, A. G., Anderson, D. E., Routzahn, K. M. and Waugh, D. S. (2001) Structural basis for oligosaccharide recognition by *Pyrococcus furiosus* maltodextrin-binding protein. *J. Mol. Biol.* 305, 891-904.

C49. Quiocho, F. A., Spurlino, J. C. and Rodseth, L. E. (1997) Extensive features of tight oligosaccharide binding revealed in high-resolution structures of the maltodextrin transport/chemosensory receptor. *Structure* 5, 997-1015.

C50. Hofnung, M., Bedouelle, H., Boulain, J. C., Clement, J. M., Charbit, A., Duplay, P., Gehring, K., Martineau, P., Saurin, W. and Szmelcman, S. (1988) Genetic approaches to the study and use of proteins: random point mutations and random linker insertions. *Bulletin de l'Institut Pasteur,* 86, 95-101.

C51. Betton, J. M., Jacob, J. P., Hofnung, M. and Broome-Smith, J. K. (1997) Creating a bifunctional protein by insertion of beta-lactamase into the maltodextrin-binding protein. *Nat. Biotechnol.* 15, 1276-1279.

C52. Betton, J. M., Martineau, P., Saurin, W. and Hofnung, M. (1993) Location of tolerated insertions/deletions in the structure of the maltose binding protein. *FEBS Lett.* 325, 34-38.

C53. Guntas, G., Mansell, T. J., Kim, J. R. and Ostermeier, M. (2005) Directed evolution of protein switches and their application to the creation of ligand-binding proteins. *Proc. Natl. Acad. Sci. USA* 102, 11224-11229.

C54. Martineau, P., Leclerc, C. and Hofnung, M. (1996) Modulating the immunological properties of a linear B-cell epitope by insertion into permissive sites of the MalE protein. *Mol. Immunol.* 33, 1345-1358.

C55. Puziss, J. W., Harvey, R. J., Bassford, P. J. Jr. (1992) Alterations in the hydrophilic segment of the maltose-binding protein (MBP) signal peptide that affect either export or translation of MBP. *J. Bacteriol.* 174, 6488-6497.

C56. Liang, J., Kim, J. R., Boock, J. T., Mansell, T. J. and Ostermeier, M. (2007) Ligand binding and allostery can emerge simultaneously. *Protein Sci.* 16, 929-937.

C57. Hecky, J. and Muller, K. M. (2005) Structural perturbation and compensation by directed evolution at physiological temperature leads to thermostabilization of beta-lactamase. *Biochemistry* 44, 12640-12654.

C58. Miller, G. L. (1959) Use of dinitrosalicylic acid reagent for determination of reducing sugars. *Anal. Chem.* 31, 426-428.

C59. Berrondo, M., Ostermeier, M. & Gray, J. J. (2008) Structure prediction of domain insertion proteins from structures of individual domains. *Structure* 16, 513-527.

C60. Jung, W. S., Hong, C. K., Lee, S., Kim, C. S., Kim, S. J., Kim, S. I. & Rhee, S. (2007) Structural and functional insights into intramolecular fructosyl transfer by inulin fructotransferase. *J. Biol. Chem.* 282, 8414-8423.

C61. Kim, K.-Y., Koo, B.-S., Jo, D. & Kim. S.-I. (2004) Cloning, expression, and purification of exoinulinase from *Bacillus* sp. Snu7. *J. Microbiol. Biotechnol.* 14, 344-349.

C62. Kim, J. R. & Ostermeier, M. (2006) Modulation of effector affinity by hinge region mutations also modulates switching activity in an engineered allosteric TEM1 beta-lactamase switch. *Arch. Biochem. Biophys.* 446, 44-51.

C63. Gill, S. C. & von Hippel, P. H. (1989) Calculation of protein extinction coefficients from amino acid sequence data. *Anal. Biochem.* 182, 319-326.

C64. Bradford, M. M. (1976) A Rapid and Sensitive Method for the Quantitation of Microgram Quantities of Protein Utilizing the Principle of Protein-Dye Binding. *Anal. Biochem.* 72, 248-254.

C65. Melius, P. (1971) Isolation of yeast invertase by sephadex gel chromatography. A biochemistry laboratory experiment. *J. Chem. Edu.* 48, 765-766.

C66. McManus-Munoz, S. & Crowder, M. W. (1999) Kinetic mechanism of metallo-beta-lactamase L1 from *Stenotrophomonas maltophilia*. Biochemistry 38, 1547-1553.

C67. Sigal, I. S., DeGrado, W. F., Thomas, B. J. & Petteway, S. R., Jr. (1984) Purification and properties of thiol beta-lactamase. A mutant of pBR322 beta-lactamase in which the active site serine has been replaced with cysteine. *J. Biol. Chem.* 259, 5327-5332.

C68. Kumar, S., Adediran, S. A., Nukaga, M. & Pratt R F. (2004) Kinetics of turnover of cefotaxime by the *Enterobacter cloacae* P99 and GCI beta-lactamases: two free enzyme forms of the P99 beta-lactamase detected by a combination of pre- and post-steady state kinetics. *Biochemistry* 43, 2664-2072.

C69. Sowek, J. A., Singer, S. B., Ohringer, S., Malley, M. F., Dougherty, T. J., Gougoutas, J. Z. & Bush, K. (1991) Substitution of lysine at position 104 or 240 of TEM-1pTZ18R beta lactamase enhances the effect of serine-164 substitution on hydrolysis or affinity for cephalosporins and the monobactam aztreonam. *Biochemistry* 30, 3179-3188.

---

What is claimed is:

1. A method for protein stabilization by domain insertion into a thermophilic protein, wherein:
the domain insertion is accomplished by insertional fusion of two distinct proteins wherein a first of the proteins is inserted into the middle of a second of the proteins to create a protein complex;
the primary sequence of the inserted first protein is not modified;
the enzymatic activity of the inserted first protein is largely maintained;
the stability of the inserted first protein is increased;
the first protein is wild-type exoinulinase (EI) and the second protein is a maltodextrin-binding protein from *Pyrococcus furiosus* (PfMBP);
the first protein is inserted between residues 125 and 126 of the second protein;
the amino acid sequence of PfMBP is (SEQ ID NO: 1)
MKIKTGARILALSALTTMMFSASALAKIEEGKVVIWHAMQPNELEVFQSL

AEEYMALCPEVEIVFEQKPNLEDALKAAIPTGQGPDLFIWAHDWIGKFAE

AGLLEPIDEYVTEDLLNEFAPMAQDAMQYKGHYYALPFAAETVAIIYNKE

MVSEPPKTFDEMKAIMEKYYDPANEKYGIAWPINAYFISAIAQAFGGYYF

DDKTEQPGLDKPETIEGFKFFFTEIWPYMAPTGDYNTQQSIFLEGRAPMM

VNGPWSINDVKKAGINFGVVPLPPIIKDGKEYWPRPYGGVKLIYFAAGIK

NKDAAWKFAKWLTTSEESIKTLALELGYIPVLTKVLDDPEIKNDPVIYGF

GQAVQHAYLMPKSPKMSAVWGGVDGAINEILQDPQNADIEGILKKYQQEI

LNNMQGHHHHHH;

and
the DNA sequence coding for PfMBP is (SEQ ID NO: 2)
atgaaaataaaaacaggtgcacgcatcctcgcattatccgcattaacgac gatgatgttttccgcctcggctctcgccaaaatcgaagaaggaaaagttg ttatttggcatgcaatgcaacccaatgagcttgaggtcttccaaagctta gcggaagaatacatggcactctgtccagaagttgagatagtttttgaaca aaagccaaacttggaagatgctcttaaggctgcaatacccacaggtcaag gtcctgacctctttatctgggctcacgactggattggaaagtttgctgag gcaggattacttgagccaattgatgaatatgtaactgaagatctccttaa cgagtttgctccaatggcccaggatgcaatgcagtataaaggtcactact atgctctaccattcgccgctgaaacagttgcaataatctacaacaaagaa atggttagcgagccaccgaaaacctttgatgagatgaaggcaataatgga gaagtactatgatccagcaaatgagaagtatggaatagcttggccaatta atgcctactttatctcagcaattgctcaggcctttggtggttactacttt gacgacaaaacagagcaacccggactagataagcctgagacaatcgaagg atttaagttcttcttcacagaaatatggccatacatggctccaactggag actacaacactcaacagagtatattcctcgagggtagagccccaatgatg gttaatggtccatggagcattaacgacgttaagaaggcaggaataaactt tggagtggttccactacctccaataatcaaggatggtaaggagtactggc caaggccttacggtggagttaagttgatttacttcgcagcgggaataaag aacaaggatgctgcatggaagttcgcaaagtggcttaccacaagcgaaga gtcaattaagacattggcactagagctgggatacataccggttcttacga aggttcttgatgatccagaaattaagaatgatccagtaatctatggcttt ggacaagcagttcagcacgcatacctaatgccaaagagtccaaagatgag tgctgtttggggcggagttgatggggcaattaacgaaatcctccaagatc cacaaaacgctgacattgaaggaatactaaagaagtatcaacaagaaatc cttaacaacatgcaaggccatcatcaccaccatcactgataa.

2. The method as claimed in claim 1, wherein the insertional fusion is achieved at a specific insertion site.

3. The method as claimed in claim 1, wherein the insertional fusion is made using recombinant DNA techniques.

4. The method as claimed in claim 1, wherein the stability of the protein complex is higher than the stability of the first protein.

5. The method as claimed in claim 4, wherein the stability is determined by measuring exoinulinase activity of the protein complex and of the first protein during fourteen days of incubation at 37° C., and by measuring concentrations of the protein complex and of the first protein in solution without being precipitated after twenty days of incubation at 37° C.

\* \* \* \* \*